(12) United States Patent
Im et al.

(10) Patent No.: US 9,924,912 B2
(45) Date of Patent: Mar. 27, 2018

(54) X-RAY IMAGE PROCESSING SYSTEM AND METHOD

(71) Applicants: VATECH Co., Ltd., Gyeonggi-do (KR); VATECH EWOO Holdings Co., Ltd., Gyeonggi-do (KR)

(72) Inventors: Se Yeol Im, Gyeonggi-do (KR); Dong Wan Seo, Gyeonggi-do (KR); Tae Hee Han, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/081,815

(22) Filed: Mar. 25, 2016

(65) Prior Publication Data
US 2016/0278721 A1     Sep. 29, 2016

(30) Foreign Application Priority Data
Mar. 27, 2015   (KR) .................. 10-2015-0043224

(51) Int. Cl.
*A61B 6/14*     (2006.01)
*A61B 6/03*     (2006.01)
*A61B 6/00*     (2006.01)
*G06T 7/62*     (2017.01)

(52) U.S. Cl.
CPC ............... *A61B 6/14* (2013.01); *A61B 6/032* (2013.01); *A61B 6/463* (2013.01); *A61B 6/466* (2013.01); *A61B 6/5217* (2013.01); *A61B 6/5235* (2013.01); *G06T 7/62* (2017.01); *G06T 2207/10081* (2013.01); *G06T 2207/20092* (2013.01); *G06T 2207/30036* (2013.01)

(58) Field of Classification Search
CPC . G06T 2207/10132; G06T 2207/30004; G06T 7/0012; G06T 2200/24; A61B 8/463; G01B 9/0203
USPC .................................................. 382/128, 134
See application file for complete search history.

(56) References Cited

U.S. PATENT DOCUMENTS

| | | | |
|---|---|---|---|
| 2010/0189308 A1* | 7/2010 | Nakatsukasa .......... | G01B 11/24 382/106 |
| 2012/0230467 A1* | 9/2012 | Katsumata ............. | A61B 6/032 378/19 |
| 2015/0279064 A1* | 10/2015 | Dennerlein .............. | G09G 5/02 382/131 |
| 2016/0012647 A1* | 1/2016 | Chen .................... | G01V 5/0008 382/203 |

* cited by examiner

*Primary Examiner* — Edward Park
(74) *Attorney, Agent, or Firm* — IP Legal Services, LLC (57) ABSTRACT

Disclosed herein is a method and apparatus for operating an X-ray image processing system of creating a panoramic image based on three-dimensional (3D) Computed Tomography (CT) image data and displaying the panoramic image on the display unit, receiving a part of an object to be measured in the panoramic image through the input unit, and calculating an actual 3D length of the part of the object based on depth information of the CT image data and displaying the actual 3D length on the display unit. The part of the object can be selected by the user to measure a length of a desired part.

9 Claims, 6 Drawing Sheets

X-RAY IMAGE PROCESSING SYSTEM AND METHOD

CROSS REFERENCE TO PRIOR APPLICATIONS

The present application claims priority under 35 U.S.C. § 119 to Korean Patent Application No. 10-2015-0043224 (filed on Mar. 27, 2015).

BACKGROUND OF THE INVENTION

1. Field of the Invention

The present invention relates to X-ray image processing, and more particularly, to a system and method for measuring and displaying the actual three-dimensional (3D) length of a part of an object, the length of which is desired to be measured, in a panoramic dental image.

2. Description of the Related Art

An X-ray imaging device used in areas of dental diagnosis may be categorized into computed tomography (CT) imaging device, a panoramic imaging device, and a cephalometric imaging device, one of which may be chosen and used depending on the purpose of examination.

Among them, panoramic imaging device is used most frequently due to the nature of dental diagnosis.

The panoramic imaging device performs X-ray scanning while following a trajectory that conforms to the form of a dental arch, with an X-ray sensor and an X-ray source arranged to face each other, and the pieces of scanned data are linked according to a certain rule such that they form a panoramic image in which the teeth and tissues surrounding the dental arch are arranged in a plane.

However, since the panoramic image acquired in this scanning method is two-dimensional (2D), it lacks image information for respective positions in the depth direction, i.e., depth information.

Moreover, the panoramic image obtained via the conventional scanning method is plagued with scanning distortion due to the characteristics thereof.

Accordingly, with the panoramic image in the scanning method, the actual length, i.e., the actual three-dimensional (3D) length of a particular object, such as a tooth, cannot be known.

SUMMARY OF THE INVENTION

Accordingly, the present invention has been made keeping in mind the above problems occurring in the prior art, and an object of the present invention is to provide a method for measuring the actual three-dimensional (3D) length of a part of an In accordance with an aspect of the present invention, there is provide an X-ray image processing method, with use of an X-ray imaging system including an input unit for receiving a user input, a display unit for displaying an X-ray image, a storage for storing X-ray image data, and a control unit for processing the X-ray image data and controlling the processing result to be displayed on the display unit, including steps: (a) creating a panoramic image based on three-dimensional (3D) Computed Tomography (CT) image data and displaying the panoramic image on the display unit, (b) receiving a part of an object to be measured in the panoramic image through the input unit, and (c) calculating an actual 3D length of the part of the object based on depth information of the CT image data and displaying the actual 3D length on the display unit.

In an embodiment, step (c) may include displaying the actual 3D length in a cross-sectional image of the part of the object in the depth direction or a cross-sectional image in a plane capable of displaying a full length of the part of the object.

In an embodiment, step (b) may further include receiving a first length measurement line on the part of the object in the panoramic image, and step (c) may further include displaying a second length measurement line of the actual 3D length on the part of the object in the cross-sectional image.

In an embodiment, step (b) may further include receiving at least one of an adjusted position, an adjusted direction, and an adjusted length of the second length measurement line through the input unit.

In an embodiment, step (c) may further include displaying the actual 3D length of the second length measurement line by the control unit.

In accordance with another aspect of the present disclosure, an X-ray image processing system may include an input unit configured to receive an user input, a display unit configured to display an X-ray image, a storage configured to store X-ray image data, and a control unit configured to process the X-ray image data for obtaining an X-ray image and display the X-ray image on the display unit, wherein the X-ray image is a panoramic image based on CT (Computed Tomography) image data, wherein the input unit receives a part of an object from the panoramic image, and wherein the control unit calculates an actual 3D (three-dimensional) length of the part of the object based on a depth information of the panoramic image using the CT image data and displays the actual 3D length on the display unit.

In an embodiment, the control unit may be configured to display a cross-sectional image of the part of the object in the depth direction or a cross-sectional image in a plane capable of displaying a full length of the part of the object on the display unit with the actual 3D length.

In an embodiment, the input unit may receive a first length measurement line on the part of the object, and the control unit may be configured to display a second length measurement line of the actual 3D length.

In an embodiment, the user input unit may receive at least one of an adjusted position, an adjusted direction, and an adjusted length of the second length measurement line.

In an embodiment, the control unit may be configured to create a depth map including the depth information for respective positions of the panoramic image for calculating the actual 3D length of the part of the object.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Embodiments of the present invention will now be described in detail with reference to accompanying drawings.

According to the embodiments, a panoramic image may be acquired by using Computed Tomography (CT) image data, which is three-dimensional (3D) X-ray image data, and the actual 3D length of a particular part of an object selected in the panoramic image may be measured and displayed. This will now be described in more detail.

Figure 1:
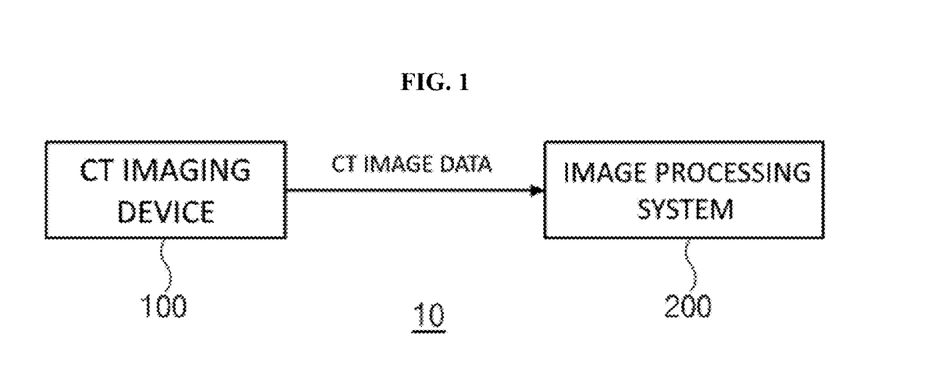
FIG. 1 is a schematic block diagram of an X-ray imaging system, according to an embodiment of the present invention.
Figure 2:
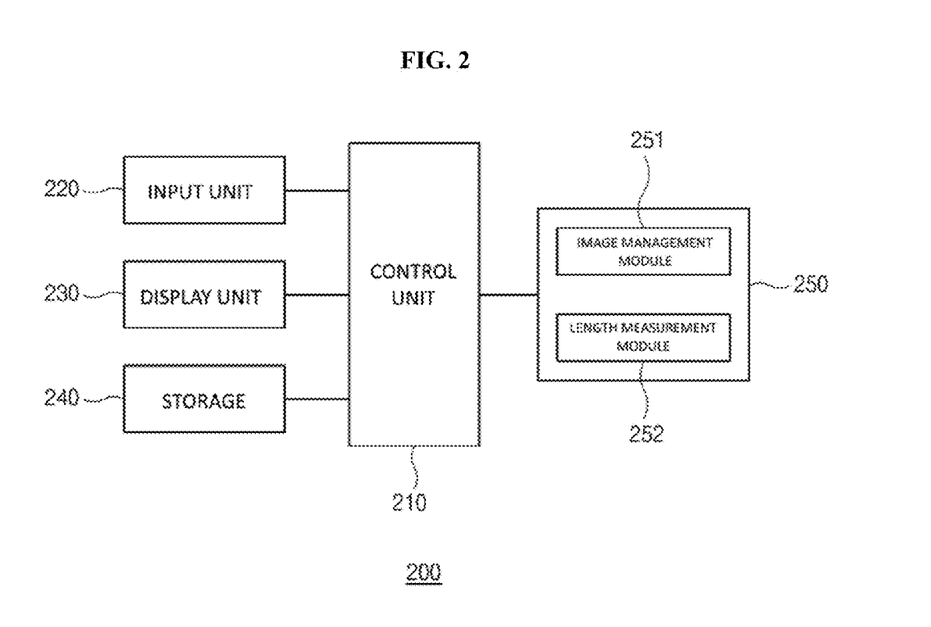
FIG. 2 is a schematic block diagram of an X-ray image processing system, according to an embodiment of the present invention.

FIG. 1 is a schematic block diagram of an X-ray imaging system, according to an embodiment of the present invention, and FIG. 2 is a schematic block diagram of an X-ray image processing system, according to an embodiment of the present invention.

Referring to FIG. 1, an X-ray imaging system 10 in accordance with an embodiment of the present invention may include a CT imaging device 100, for performing X-ray CT imaging and acquiring resultant 3D CT image data, and an X-ray image processing system 200 for processing the CT image data to create various cross-sectional images as well as a panoramic image.

A cone beam CT imaging device may be used for the CT imaging device 100. CT image data scanned and generated by the CT imaging device 100 may be sent to the X-ray image processing system 200.

The X-ray image processing system 200 may use the CT image data sent from the CT imaging device 100 to create and display a 3D CT image and at least one two-dimensional (2D) cross-sectional image in the 3D CT image. The cross-sectional image may be reconstructed through Multi-planar Reformation (MPR).

Furthermore, the X-ray image processing system 200 may use the CT image data to create and display a panoramic image of a dental arch. For this, the user may designate or select a certain image layer for a panoramic image in the 3D CT image and/or the at least one cross-sectional image, and the X-ray image processing system 200 may create and display the panoramic image by reconstructing a cross-sectional image for the image layer.

In particular, such a panoramic image may be created based on the 3D CT image data, and a depth map, a map about image information for each position in the depth direction, i.e., depth information, may be generated when creating the panoramic image. This enables the actual length of a particular part in the panoramic image to be accurately measured.

For example, a system like a computer may be used as the X-ray image processing system 200 for performing such functions.

The X-ray image processing system 200 may include a control unit 210, an input unit 220, a display unit 230, a storage 240, and an image processing unit 250.

The control unit 210 is a central processing unit that controls the overall operation of the components of the X-ray image processing system 200.

In an embodiment, the control unit 210 may be implemented by at least one of Application Specific Integrated Circuits (ASICs), Digital Signal Processors (DSPs), Digital Signal Processing Devices (DSPDs), Programmable Logic Devices (PLDs), Field-Programmable Gate Arrays (FPGAs), processors, controllers, micro-controllers, and microprocessors. The control unit 210 may also be implemented in firmware/software modules that may be executed on the aforementioned hardware. In this case, the firmware/software modules may be implemented by one or more software applications written in appropriate programming languages.

The input unit 220 may be a means for the user to manipulate the X-ray image processing system 200.

In an embodiment, the input unit 220 may include a keyboard, a keypad, a touch pad, a mouse, etc., but is not limited thereto. For example, the input unit 220 may include a Graphic User Interface (GUI) that may be controlled with the aforementioned input means.

The display device 230 may be a means for displaying 3D CT images, at least one cross-sectional image, panoramic images, etc., processed by the X-ray image processing system 200.

In an embodiment, the display unit 230 displays various X-ray images created according to various embodiments of the present invention, and may include various display devices, such as a Liquid Crystal Display (LCD), a Light Emitting Diode (LED) display, an Active Matrix Organic LED (AMOLED) display, a Cathode Ray Tube (CRT) display, etc.

The storage 240 may store CT image data, input into the X-ray image processing system 200, and various types of image data processed by the X-ray image processing system 200. The storage 240 may also store an image processing application that constitutes the image processing unit 250.

In an embodiment, the storage 240 may be used to store image data obtained in the course of image processing in accordance with various embodiments of the present invention, image data resulting from image processing in accordance with various embodiments of the present invention, and variables required to perform image processing in accordance with various embodiments of the present invention.

In various embodiments, the storage 240 may store the aforementioned images in a Digital Imaging and Communications in Medicine (DICOM) format, or in a general common image file format, such as BMP, JPEG, TIFF, or the like. The storage 240 may further store software/firmware required to implement the control unit 210. The storage 240 may be implemented with one of a flash memory, a hard disk, a Multi-Media Card (MMC), a card-type memory, e.g. a Secure Digital (SD) card or an eXtream Digital (XD) card, a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk, but it is obvious to an ordinary skilled person in the art that it is not limited thereto.

The image processing unit 250 is an essential feature for performing image processing and length measurement in accordance with embodiments of the present invention, and may be implemented as a combination of logic circuits for performing computation and an image processing application for driving the logic circuits to perform information processing.

In an embodiment, the image processing unit 250 may be incorporated in the control unit 210, or part of the image processing unit 250 may be stored in the storage 240.

The image processing unit 250 may be configured to include an image management module 251 and a length measurement module 252. The image processing unit 250 may provide a panoramic image creation tool, for performing a panoramic image creation function, and a length measurement tool for performing a length measurement function.

In an embodiment, the panoramic image creation tool may cooperate with the image management module 251 to display a 3D CT image and/or at least one cross-sectional image on the display unit 230, and once a certain image layer is designated or selected for the 3D CT image and/or the at least one cross-sectional image, the panoramic image creation tool may create and display a panoramic image by reconstructing the cross-sectional image for the image layer.

The image management module 251 is configured to process and manage an image to be displayed on the display unit 230, and uses the CT image data stored in the storage 240 to create a 3D CT image, at least one cross-sectional image, a panoramic image, etc., upon a request from the user. Furthermore, the image management module 251 may perform overall screen display management so as to display a created image in a corresponding view, i.e., a window on the display unit 230.

Figure 3:
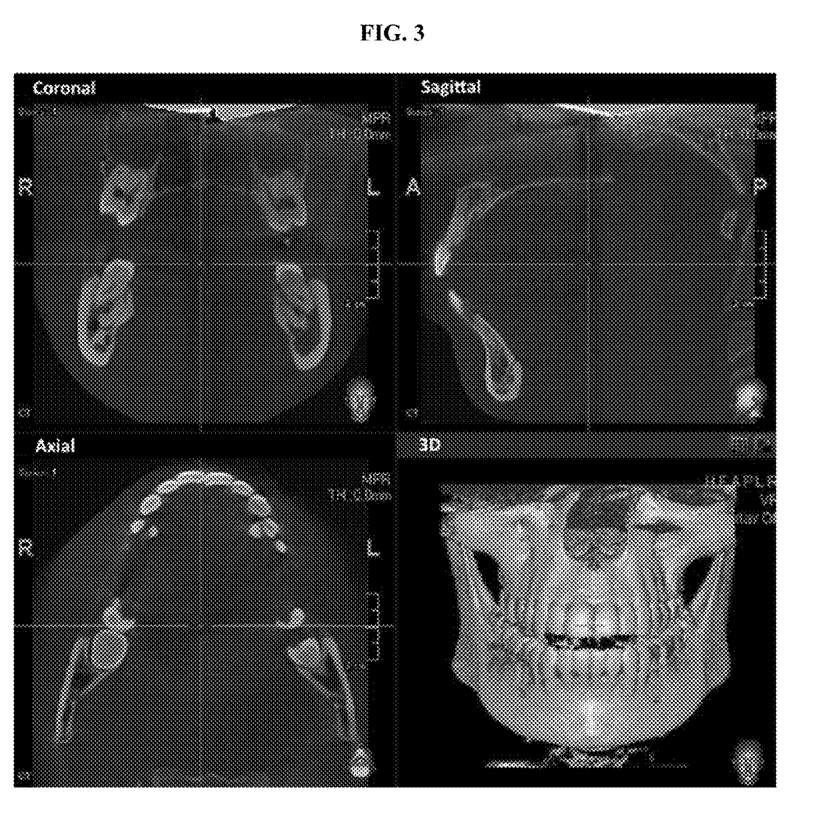
FIG. 3 shows an example of a Computed Tomography (CT) image and cross-sectional images generated by an X-ray image processing system, according to an embodiment of the present invention.

In this regard, for example, the image management module 251 may basically manage the 3D CT image and at least one cross-sectional image, e.g., coronal, sagittal, or axial cross-sectional images to be displayed on the respective windows, as shown in FIG. 3.

Figure 4:
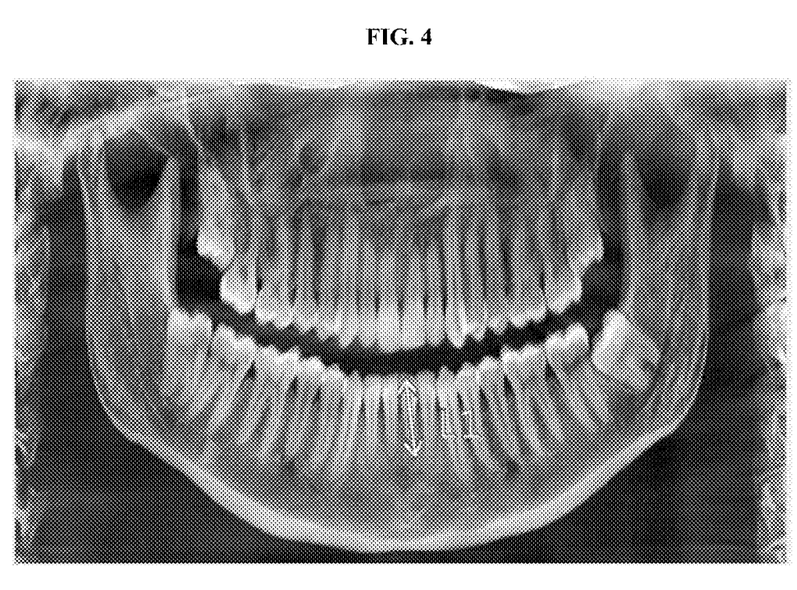
FIG. 4 shows an example of a panoramic image generated by an X-ray image processing system, according to an embodiment of the present invention.

With the screen shown in FIG. 3, the user may request panoramic image display by manipulating the input unit 220, and in response, the image management module 251 may use the CT image data to create a panoramic image as shown in FIG. 4 and control a window to display the panoramic image in popup form on the screen or to be displayed in a suitable window. At this time, at least part of the 3D CT image and the cross-sectional image may be controlled so as not to be displayed on the screen.

In this way, the image management module 251 may manage the creation of various images and the status of the window display on the screen.

In the meantime, the image management module 251 may manage information about the created image to be stored in the storage 240.

The length measurement module 252 may be configured to compute and measure the actual length of a particular part of an object in the panoramic image.

In this regard, for example, the user may select and mark the particular part, e.g. a tooth part, for length measurement in the panoramic image on the screen.

For this, the user may use the input unit 220, such as a mouse, to draw a line or designate starting and ending points on the particular part for length measurement on the screen of the panoramic image. In response to a user action, a length measurement line L1 such as that shown in FIG. 4 may be displayed on the panoramic image. Herein, for convenience of explanation, the length measurement line L1 displayed on the panoramic image will be called a first length measurement line.

In response to such a user request, the length measurement module 252 may use CT image data to calculate the actual 3D length of the selected part of the object. For example, depth information of a depth map about the part of the object required for length measurement may be used to calculate the actual 3D length of the selected part of the object by calculating the 3D positions of starting and ending points of the part of the object and then the actual 3D distance between the 3D positions. In an embodiment, the actual 3D distance between the starting and ending points may be the shortest distance in 3D.

The actual 3D length measured by the length measurement module 252 may be displayed on a cross-sectional image of the part of the object.

Figure 5:
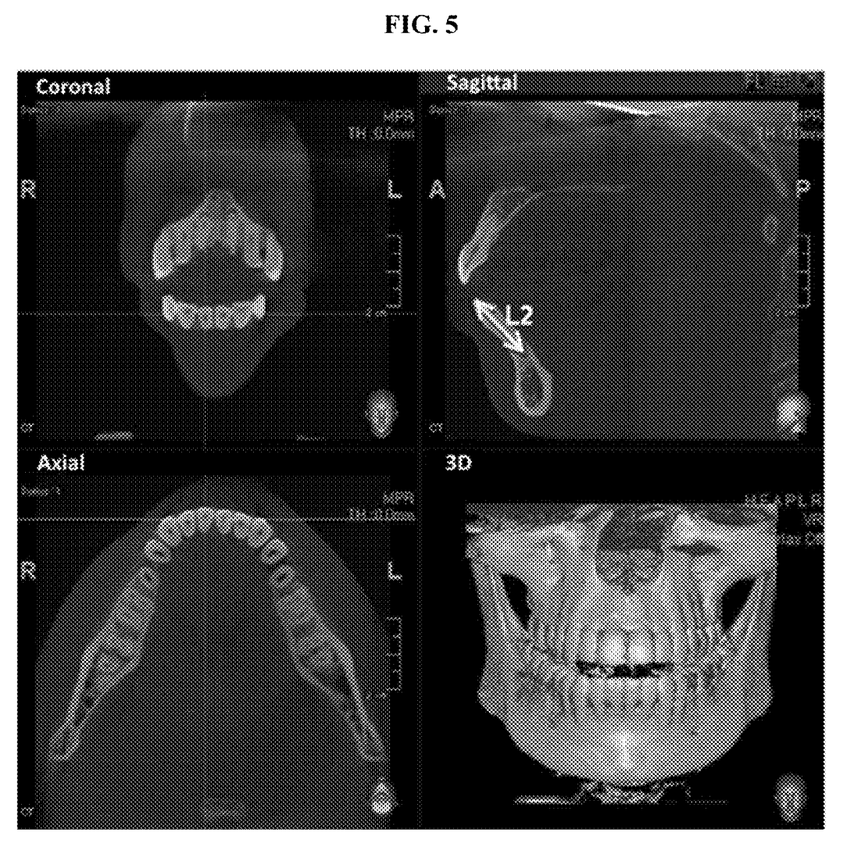
FIG. 5 shows a CT image and cross-sectional images corresponding to a part of an object selected for length measurement in the panoramic image of FIG. 4.

For this, in response to the request of the user for length measurement, the image management module 251 may manage at least one cross-sectional image containing the selected part of the object to be displayed on the screen, as shown in FIG. 5. With respect to the panoramic image, an actual 3D length measurement line L2, i.e., a second length measurement line L2 corresponding to the first length measurement line L1, may be displayed on a sagittal cross-sectional image, which is a cross-sectional image in the depth direction of the part of the object, and the actual length of the second length measurement line L2 may also be displayed in numerical form on a suitable part of the screen. Although not shown in the drawings, the actual 3D length measurement line L2, i.e. the second length measurement line L2 corresponding to the first length measurement line L1, may be displayed not only on the sagittal cross-sectional image but also on at least one of coronal and axial cross-sectional images, and the actual length of the second length measurement line L2 may also be displayed in numerical form on a suitable part of the screen.

Figure 6:
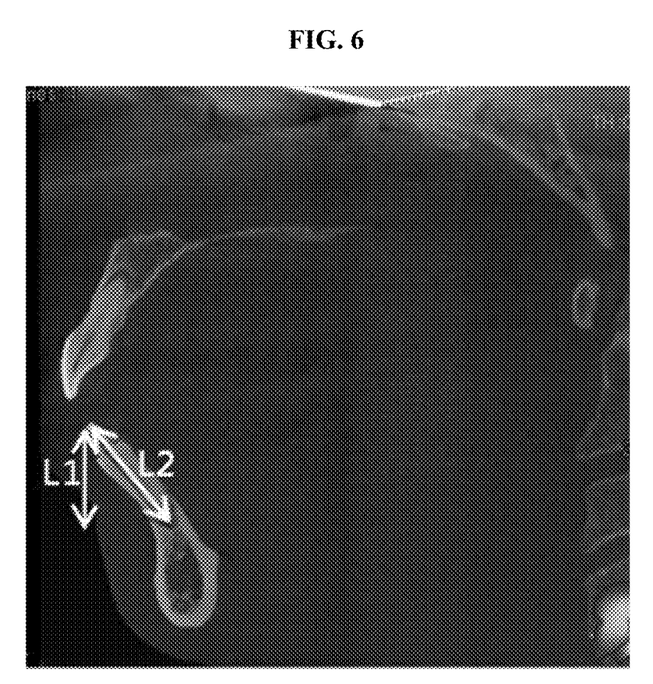
FIG. 6 shows the relationship between a length measurement line of the panoramic image of FIG. 4 and an actual length measurement line of the cross-sectional image of FIG. 5.

The first and second length measurement lines L1 and L2 will now be described with reference to the sagittal cross-sectional image shown in FIG. 6. A panoramic image created using CT image data resulting from X-ray scanning is orthogonal to the sagittal cross-sectional image, so the first length measurement line L1, displayed on the panoramic image, is directed in the height direction, i.e., in the vertical direction on the sagittal cross-sectional image, as shown in FIG. 6. The actual part of the object corresponding to the first length measurement line L1 actually has an inclined form made by extending the starting and ending points of the first length measurement line L1 horizontally across the sagittal plane to the image layer of the panoramic image and connecting them, as shown in FIG. 6.

Depth information of the part of the object may then be applied in order to display the second length measurement line L2 on the image layer of the panoramic image corresponding to the first length measurement line L1 on the part of the object in the sagittal cross-sectional image.

The second length measurement line L2 may be calculated by a vector operation on the depth information of the part of the object for the first length measurement line L1.

As such, the user may conveniently and visually check the length measurement result using the cross-sectional image of the part of the object, provided in response to the request of the user for length measurement in the panoramic image.

While the sagittal cross section was taken as an example in the above description, the embodiments of the present invention will be equally applied to the axial and/or coronal cross sections.

Furthermore, in addition to the coronal, sagittal, and axial cross-sectional images, it is also possible to display a cross-sectional image of a plane containing the second length measurement line L2. In the plane, the second length measurement line L2 may be displayed in a full length, and the user may check an object on the screen corresponding to the actual length of the second length measurement line L2.

Further, the position, direction, and length of the length measurement line L2 may be adjusted by the user in the cross-sectional image of the part of the object, thereby an actual 3D length can be displayed. Accordingly, the user may correct errors in the length measurement.

As such, user convenience and accuracy in length measurement may be maximized by providing the cross-sectional image corresponding to a part for which a length measurement is required and allowing error correction of length in the cross-sectional image.

Figure 7:
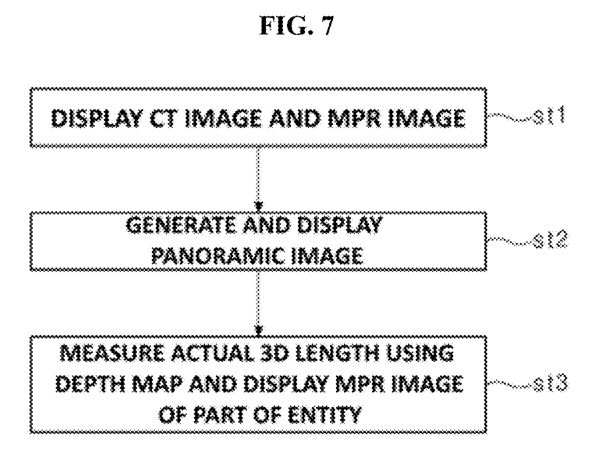
FIG. 7 is a flowchart illustrating a method for measuring the length of an object in a panoramic image, the method performed by an X-ray image processing system, according to an embodiment of the present invention.

According to an embodiment of the present invention, referring to FIG. 7, a method for measuring the length of an object in a panoramic image which is performed by the X-ray image processing system will now be described.

First, a 3D CT image and/or at least one cross-sectional image may be displayed on a screen of a display device by receiving and processing CT image data created by a CT imaging device, in step st1.

Next, in response to a request from a user to create a panoramic image, the panoramic image is created based on the CT image data and displayed on the screen, in step st2. While creating the panoramic image, a depth map containing the depth information may be generated.

Next, in response to a request of the user to measure the length of a particular part of an object in the panoramic image, the depth map is used to measure the actual length of the part of the object, and cross-sectional images of the part of the object are created and displayed in step st3. At this time, a length measurement line is displayed in a cross-sectional image corresponding to the depth direction of the part of the object or in a cross-sectional image of a plane that may display the actual length.

As described above, according to embodiments of the present invention, a panoramic image may be acquired by using CT scanned data, such that the actual 3D length of a particular part of an object may be accurately measured and calculated in response to a request for a length measurement of the part of the object in the panoramic image.

Furthermore, user convenience and accuracy in length measurement may be maximized by providing a cross-sectional image corresponding to a part for which a length measurement is required and allowing error correction on the cross-sectional image.

In the meantime, the method for operating the X-ray image processing system in accordance with the embodiments of the present invention may be recorded on a computer-readable medium, e.g., a magnetic medium, such as a hard disk, a floppy disk, and a magnetic tape, an optical medium, such as a compact disc ROM (CD-ROM) and a digital versatile disk, a magneto-optical medium, such as a floptical disk, a ROM, a RAM, a flash memory, etc. According to embodiments of the present invention, a panoramic image may be acquired by using CT image data, such that the actual 3D length of a particular part of an object may be accurately measured upon request in the panoramic image.

According to embodiments of the present invention, a panoramic image may be acquired using CT image data, such that the actual 3D length of a particular part of an object may be accurately measured on the user's request in the panoramic image.

Furthermore, the cross-sectional image that may best represent the actual 3D length of the part of the object may be provided, and error correction may be allowed in the cross-sectional image, thereby maximizing user convenience and length measurement accuracy.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An X-ray image processing method with use of an X-ray imaging system including an input unit for receiving a user input, a display unit for displaying an X-ray image, a storage for storing X-ray image data, and a control unit for processing the X-ray image data and controlling the processing result to be displayed on the display unit, comprising steps:
    (a) creating a panoramic image based on three-dimensional (3D) Computed Tomography (CT) image data and displaying the panoramic image on the display unit;
    (b) receiving a part of an object to be measured in the panoramic image through the input unit; and
    (c) calculating an actual 3D length of the part of the object based on a depth map including depth information of the CT image data and displaying, on the display unit, the actual 3D length in a cross-sectional image of the part of the object in a depth direction or a cross-sectional image in a plane capable of displaying a full length of the part of the object in the depth direction,
    wherein the depth map including the depth information is created for respective positions of the panoramic image for calculating the actual 3D length of the part of the object.

2. The X-ray image processing method of claim 1,
    wherein step (b) further includes receiving a first length measurement line on the part of the object in the panoramic image, and
    wherein step (c) further includes displaying a second length measurement line of the actual 3D length on the part of the object in the cross-sectional image.

3. The X-ray image processing method of claim 2,
    wherein step (b) further includes receiving at least one of an adjusted position, an adjusted direction, and an adjusted length of the second length measurement line through the input unit, and
    wherein step (c) further includes displaying the actual 3D length of the second length measurement line by the control unit.

4. The X-ray image processing method of claim 1, wherein the cross-sectional image includes at least one of a coronal cross-sectional image, a sagittal cross-sectional image, and an axial cross-sectional image.

5. An X-ray image processing system comprising:
    a storage configured to store X-ray image data;
    a display device configured to display an X-ray image; and
    at least one hardware image processor which executes:
        an input unit configured to receive a user input through a user interface; and
        a control unit configured to process the X-ray image data for obtaining the X-ray image to be displayed according to the user input and display the X-ray image on the display device, wherein the X-ray image is a panoramic image based on Computed Tomography (CT) image data, wherein the input unit receives a part of an object from the panoramic image, and wherein the control unit calculates an actual three-dimensional (3D) length of the part of the object based on depth map including a depth information of the panoramic image using the CT image data and displays, on the display device, the actual 3D length in a cross-sectional image of the part of the object in a depth direction or a cross-sectional image in a plane capable of displaying a full length of the part of the object in the depth direction, wherein the depth map including the depth information is created for respective positions of the panoramic image for calculating the actual 3D length of the part of the object.

6. The X-ray image processing system of claim 5, wherein the input unit receives a first length measurement line on the part of the object, and wherein the control unit is configured to display a second length measurement line of the actual 3D length on the part of the object in the cross-sectional image.

7. The X-ray image processing system of claim 6, wherein the user input unit receives at least one of an adjusted position, an adjusted direction, and an adjusted length of the second length measurement line.

8. The X-ray image processing system of claim 5, wherein the cross-sectional image includes at least one of a coronal cross-sectional image, a sagittal cross-sectional image, and an axial cross-sectional image.

9. An X-ray image processing system comprising:

a storage configured to store X-ray image data;

a display device configured to display an X-ray image; and at least one hardware image processor which executes:

an input unit configured to receive a user input through a user interface; and     a control unit configured to process the X-ray image data for obtaining the X-ray image to be displayed according to the user input and display the X-ray image on the display device, wherein the X-ray image is a panoramic image based on Computed Tomography (CT) image data, wherein the input unit receives a part of an object from the panoramic image, wherein the control unit calculates an actual three-dimensional (3D) length of the part of the object based on a depth map including a depth information of the panoramic image using the CT image data and displays, on the display device, the actual 3D length in a cross-sectional image of the part of the object in a depth direction or a cross-sectional image in a plane capable of displaying a full length of the part of the object in the depth direction, and wherein the control unit is configured to create the depth map including the depth information for respective positions of the panoramic image for calculating the actual 3D length of the part of the object.

* * * * *